United States Patent
Manginell et al.

(10) Patent No.: US 6,699,392 B1
(45) Date of Patent: Mar. 2, 2004

(54) METHOD TO FABRICATE SILICON CHROMATOGRAPHIC COLUMN COMPRISING FLUID PORTS

(75) Inventors: Ronald P. Manginell, Albuquerque, NM (US); Gregory C. Frye-Mason, Cedar Crest, NM (US); Edwin J. Heller, Albuquerque, NM (US); Douglas R. Adkins, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 78 days.

(21) Appl. No.: 10/167,238

(22) Filed: Jun. 10, 2002

(51) Int. Cl.[7] ............................................. B01D 15/08
(52) U.S. Cl. ...................... 210/656; 210/198.2; 95/82; 96/101
(58) Field of Search ................................ 210/635, 656, 210/198.2; 95/82; 96/101

(56) References Cited

U.S. PATENT DOCUMENTS

| | | | | | |
|---|---|---|---|---|---|
| 4,891,120 | A | * | 1/1990 | Sethi et al. | 204/600 |
| 5,116,495 | A | * | 5/1992 | Prohaska | 210/198.2 |
| 5,132,012 | A | * | 7/1992 | Miura et al. | 210/198.2 |
| 5,935,430 | A | * | 8/1999 | Craig | 210/198.2 |
| 6,171,378 | B1 | * | 1/2001 | Manginell et al. | 96/143 |

OTHER PUBLICATIONS

US 5,792,043, 8/1998, Craig (withdrawn)*

* cited by examiner

Primary Examiner—Ernest G. Therkorn
(74) Attorney, Agent, or Firm—Brian W. Dodson

(57) ABSTRACT

A new method for fabricating a silicon chromatographic column comprising through-substrate fluid ports has been developed. This new method enables the fabrication of multi-layer interconnected stacks of silicon chromatographic columns.

9 Claims, 5 Drawing Sheets

METHOD TO FABRICATE SILICON CHROMATOGRAPHIC COLUMN COMPRISING FLUID PORTS

GOVERNMENT RIGHTS

This invention was made with Government support under Contract DE-AC04-94AL85000 awarded by the U.S. Department of Energy. The Government has certain rights in the invention.

FIELD OF THE INVENTION

The present invention relates generally to microfabricated silicon chromatographic columns, and more specifically to methods to fabricate microfabricated silicon chromatographic columns with through-substrate fluid ports.

BACKGROUND OF THE INVENTION

Chromatographic columns are an important part of many chemical and biological detector systems. Prior art chromatographic columns have been manufactured in silicon substrates using techniques closely related to those of the integrated circuit industry.

A prior art silicon chromatographic column is shown in FIG. 1. In such prior art silicon chromatographic columns, a Bosch-etched trough 101, typically in the shape of a spiral with a rectangular cross-section, is formed in a silicon substrate 100. The trough is typically some tens of microns in width, some hundreds of microns in depth, and has a total length on the order of a meter. A thin stationary phase (not shown) can be added to the surface of the trough to enhance the separating properties of the final chromatographic column. The open side of the trough is then typically covered with a glass lid 102, thereby converting the trough into a long spiral column. The glass lid is often composed essentially of a Pyrex glass. The glass lid can be bonded to the silicon substrate using a variety of techniques, but is preferentially attached by anodic bonding.

Note that the glass lid 102 is shown as considerably thicker than is silicon substrate 100. This is typical of this type of prior art chromatographic column. The silicon substrate is significantly weakened by the formation of the trough 101, and the additional thickness of the glass lid is needed to obtain a product sufficiently robust for the desired applications. In this example, fluid access to the spiral column is provided by access ports 103 and 104 which penetrate glass lid 102.

Such a prior art silicon chromatographic column has multiple advantages over more conventional chromatographic columns, which typically take the form of millimeter-diameter tubes having a length of several meters. For example, whereas a conventional gas chromatograph can ramp in temperature at a typical rate of 10–20° C. per minute, this requires a heater power of hundreds of watts. The prior art silicon chromatographic columns can ramp in temperature an order of magnitude more rapidly with a heater input which is two orders of magnitude smaller. Such columns enable a rapid, portable, and low-power detector.

However, prior art silicon chromatographic columns can be improved upon. For structural integrity and ease of manufacture, the glass lid must be rather thick, typically on the order of a millimeter. As a result, the glass lid is usually the largest contributor to the heat capacity of the silicon chromatographic column. In addition, the prior art silicon chromatographic column has an extremely large surface area to volume ratio, owing to the flat and single-layer configuration. Both these features act to increase the power requirements of a detector system which comprises such columns.

An additional limitation of prior art chromatographic columns is their column length. While sufficient for some purposes, for others a column length considerably in excess of one meter is beneficial. Typical conventional gas chromatographs, for example, have column lengths of about 5–20 meters.

All of the above concerns can be addressed by forming an interconnecting stack of silicon chromatographic columns. The stacking of individual silicon chromatographic columns atop each other allows thinner glass lids to be used between them, as such a stack is stronger than is an individual silicon chromatographic column. As a result, the heat capacity of the stacked columns is less than the heat capacity of the same number of columns which are not stacked. Formation of a stack also favorably alters the surface area to volume ratio, thereby reducing average heat losses to the environment.

Finally, if the individual silicon chromatographic columns are properly interconnected, it is possible to form a longer combined column. Alternately, it is possible to connect several columns in parallel, each column having access to the same sample material. In this case, the aim can be to increase throughput of the chromatograph, or can be to perform several different chromatographic separations simultaneously.

Successfully forming such a stack of individual silicon chromatographic columns is a task made easier if fluid ports can be formed through the silicon substrate, thus allowing interconnections between the columns to be made within the material of the stack. Alternate procedures involve making external connections between the individual silicon chromatographic columns, and such connections are both difficult to make and lack physical robustness. A minimum of two through-substrate fluid ports are required for each individual silicon chromatographic column: one at the inlet of the column and the other at the output of the column.

FIG. 2 shows an individual silicon chromatographic column with multiple fluid ports. Chromatographic trough 201 is fabricated in a first surface of silicon substrate 200. Through-substrate fluid ports 202, 203, 204, and 205 provide access to the outer part of chromatographic trough 201, while through-substrate fluid port 206 provides access to the inner part of chromatographic trough 201. A glass lid (not shown) is then placed atop said first surface of silicon substrate 200 to convert chromatographic trough 201 into a chromatographic column. Access to said chromatographic column can be obtained through fluid ports 202–206, as needed for a particular application.

An implementation of a stack comprising two levels of individual silicon chromatographic columns is shown in FIG. 3. Here fluid input 300 provides access to fluid port 303 in first silicon chromatographic column 302. Fluid port 303 connects to the outer portion of first chromatographic trough 304. Fluid port 305 does not connect to first chromatographic trough 304, but rather pierces first silicon chromatographic column 302. Fluid output 301 connects to fluid port 305.

Pyrex cap 306 is affixed atop first silicon chromatographic column 302, so that cap port 307 connects to the central portion of first chromatographic trough 304. Cap port 308 is positioned so that it connects to fluid port 305.

Second silicon chromatographic column 309, which comprises second chromatographic trough 310 is affixed atop Pyrex cap 306. Fluid port 311 is formed so that it connects to the central portion of second chromatographic trough 310 and to cap port 307. Fluid port 312 is formed so that it connects to the outer portion of second chromatographic trough 304 and to cap port 308. Finally, Pyrex cap 313 is affixed atop second silicon chromatographic column 309.

In use, carrier fluid is pumped into fluid input 300. The fluid then passes through the length of first chromatographic trough 304, which has been converted into a chromatographic column by the affixing of Pyrex cap 306. The fluid then passes through cap port 307 in Pyrex cap 306, and then into second chromatographic trough 310 through fluid port 311. The fluid passes through the length of second chromatographic trough 310, then passes through fluid port 312, cap port 308, and fluid port 305 to exit the stacked chromatographic structure through fluid output 301. The fluid passing through fluid output 301 is ten directed to the desired detection, separation, or collection apparatus, which is not shown.

Due to the crystal structure of silicon and the high aspect-ratio of the desired spiral chromatographic trench, the trench must be fabricated in the silicon substrate using Bosch etching. The fluid ports can be formed using Bosch etching or wet etching, but are beneficially formed prior to the Bosch etching of the spiral chromatographic trench.

However, Bosch etching uses helium cooling gas on the side of the silicon substrate not being etched to prevent distortion and damage of the substrate during the etching process. Hence, a gas-tight seal must be maintained across the thickness of the substrate, a requirement which is incompatible with the desired result of forming a spiral chromatographic trench which connects to a fluid port through the substrate.

There is an ongoing need in the art to fabricate an individual silicon chromatographic column comprising at least one through-substrate fluid port. The instant invention provides a suitable fabrication process for this need. Other benefits of the instant invention will become clear to one skilled in the art.

SUMMARY OF THE INVENTION

A method for fabrication of silicon chromatographic columns has been developed, wherein this method comprises fabrication of through-substrate fluid ports, thereby allowing easy access of carrier fluids to the chromatographic columns, and also enabling the fabrication of multi-level interconnected stacks of silicon chromatographic columns.

BRIEF DESCRIPTION OF THE DRAWINGS

FIG. 5 shows a series of schematic views of intermediate structures in the fabrication, according to the instant invention, of a fluid port through a silicon substrate.

DETAILED DESCRIPTION

Figure 1A:
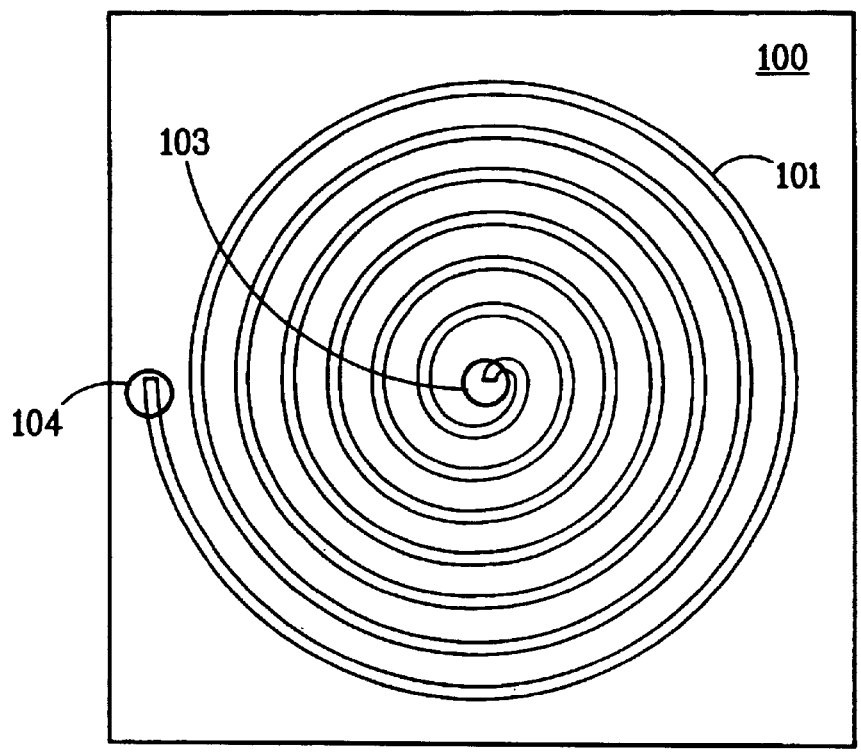
FIG. 1 shows a schematic view of a prior art silicon chromatographic column.
Figure 1B:
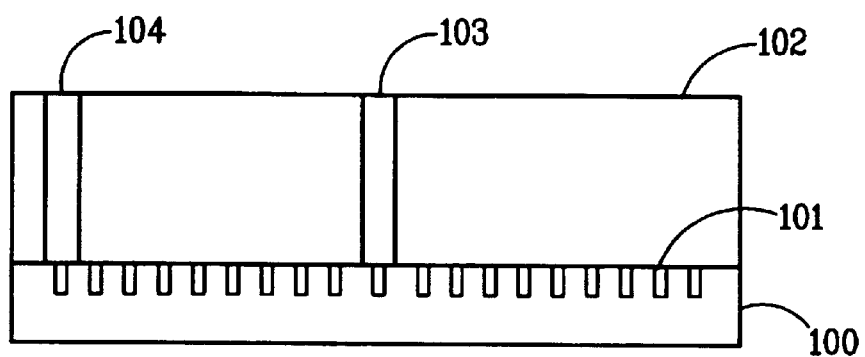
Figure 2A:
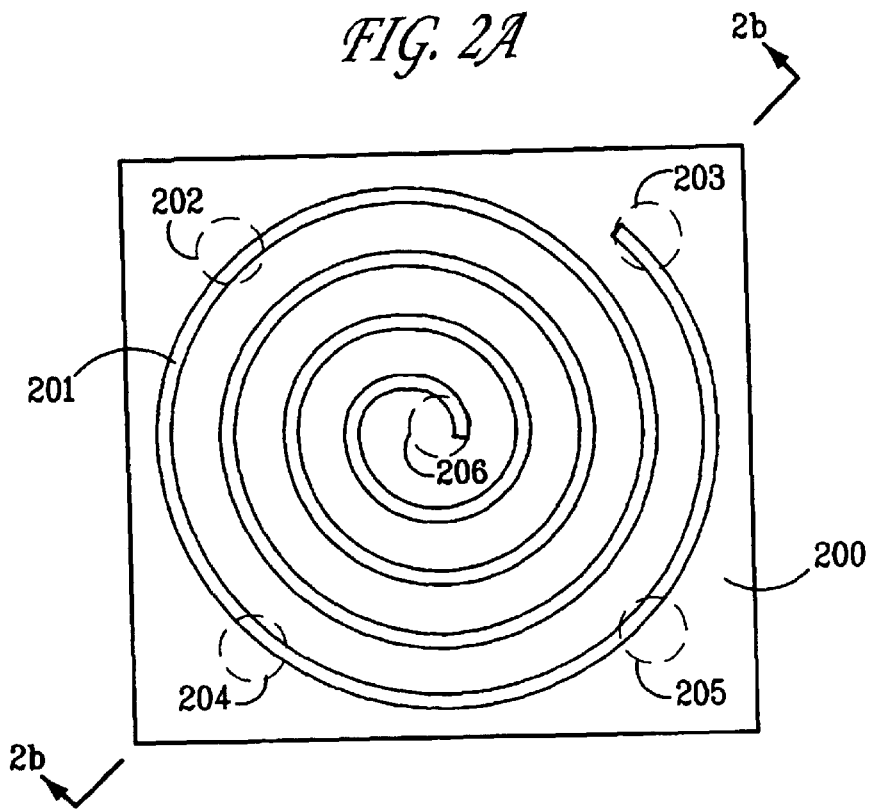
FIG. 2 shows a schematic view of a silicon chromatographic column having multiple fluid ports.
Figure 2B:
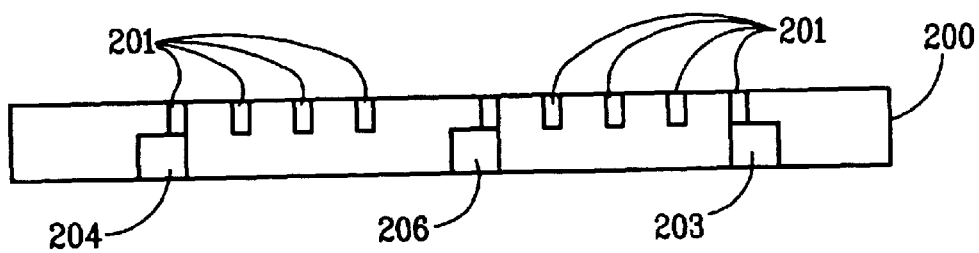
Figure 3:
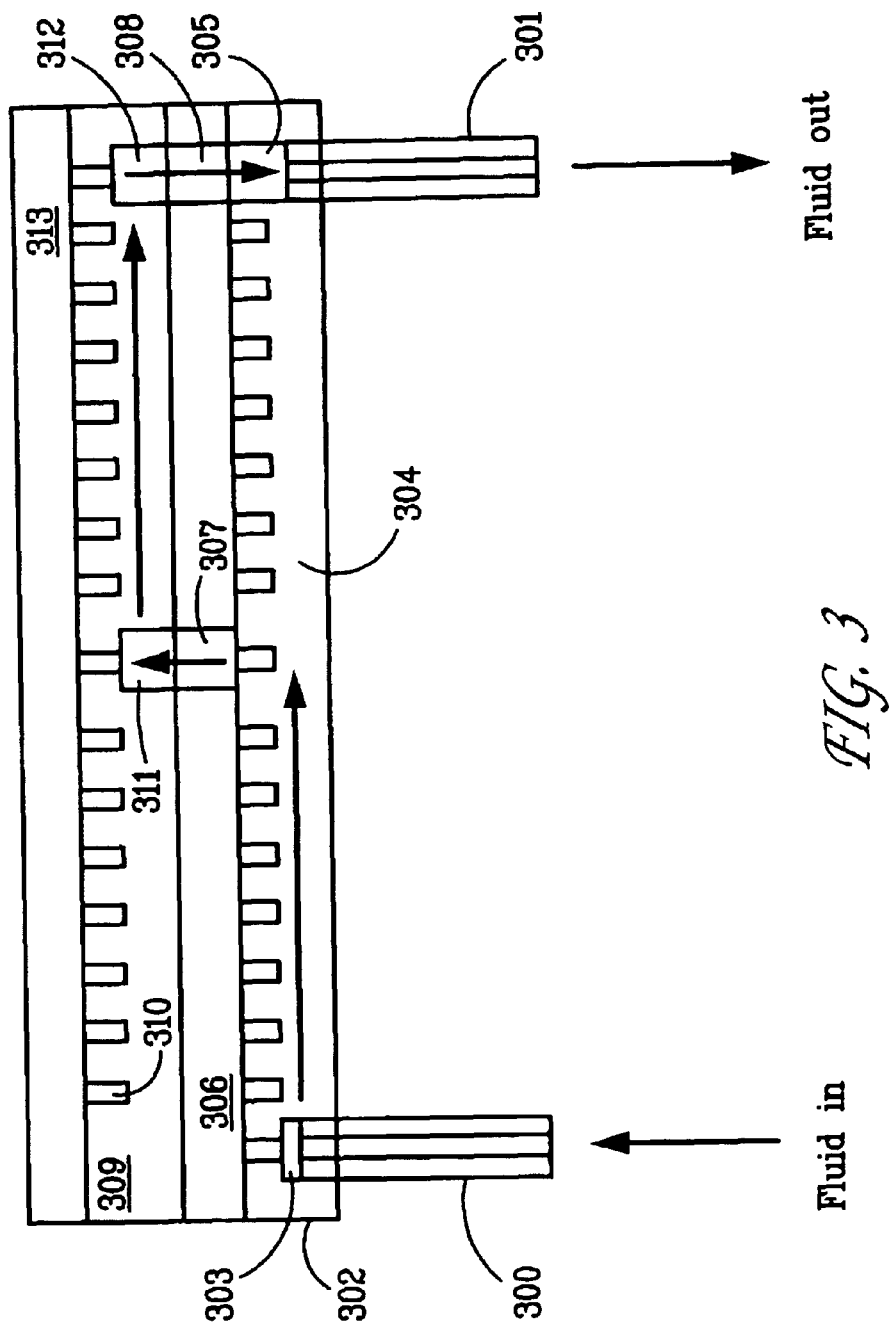
FIG. 3 shows a schematic view of an interconnected stacked silicon chromatographic column.
Figure 4:
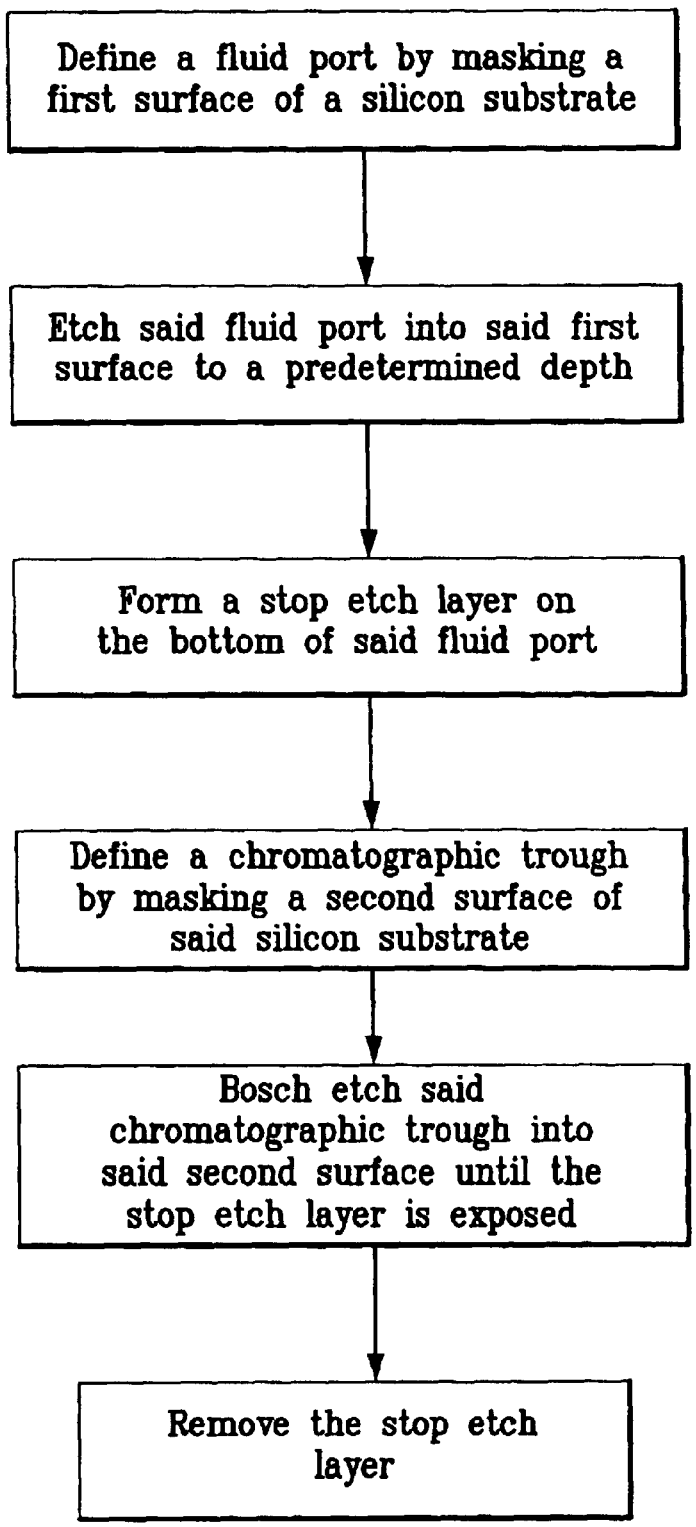
FIG. 4 shows a schematic flow diagram for an implementation of the instant invention.

A flow diagram for an implementation of the instant invention appears in FIG. 4. A series of intermediate structures which result from fabrication according to the flow diagram of FIG. 4 appear in FIG. 5. Discussion of this implementation is not intended to be limiting, but rather to illustrate key features of the instant invention.

Figure 5A:
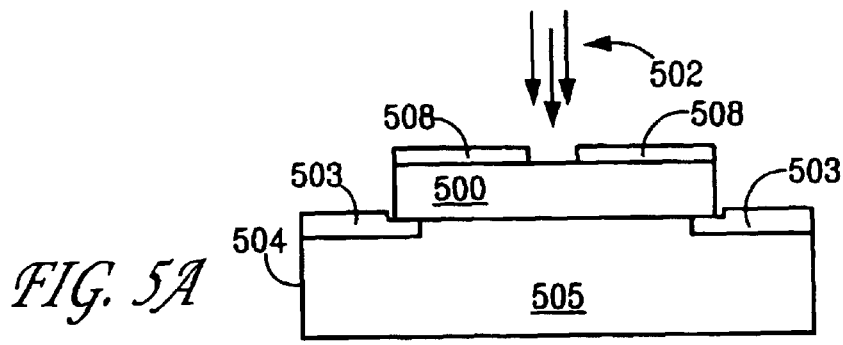
FIG. 5a shows the structure prior to Bosch etching the fluid port.
Figure 5B:
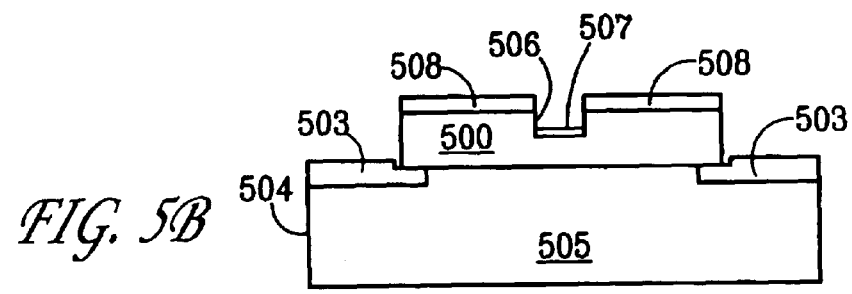
FIG. 5b shows the structure after the fluid ports have been formed, and a stop etch layer deposited in the fluid port.

As shown in FIG. 4, the first step of the process of the instant invention is to define a fluid port on a first surface of a silicon substrate by masking that first surface prior to an etching step. The corresponding structure is shown in FIG. 5a, where mask layer 501 is placed on silicon substrate 500. Silicon substrate 500 is mounted in substrate mount 503. Helium coolant gas 505 is held against a second surface of the silicon substrate 500 by chamber 504.

As shown in FIG. 4, the next step in the process of the instant invention is etching the fluid port into the first surface of the silicon substrate to a predetermined depth. This predetermined depth is generally set by the thickness of the substrate and the desired depth of the chromatographic trench to be formed in the second surface of the silicon substrate. In the implementation shown here, Bosch etch beam 502 is directed against the first surface of silicon substrate 500 to carry out the etching of the fluid port. Other etching techniques can be substituted for the Bosch etch in this step.

As shown in FIG. 4, the next step in the process of the instant invention is to form a stop etch layer in the bottom of the etched fluid port. This gives the structure shown in FIG. 5b, where a stop etch layer 507 has been formed at the bottom of the fluid port 506 which has been etched in the previous process step. The stop etch layer is beneficially formed of a silicon oxide, but can also take the form of a ceramic or metallic thin film, or alternately can take the form of a polymer layer, for example composed essentially of a photoresist material.

Figure 5C:
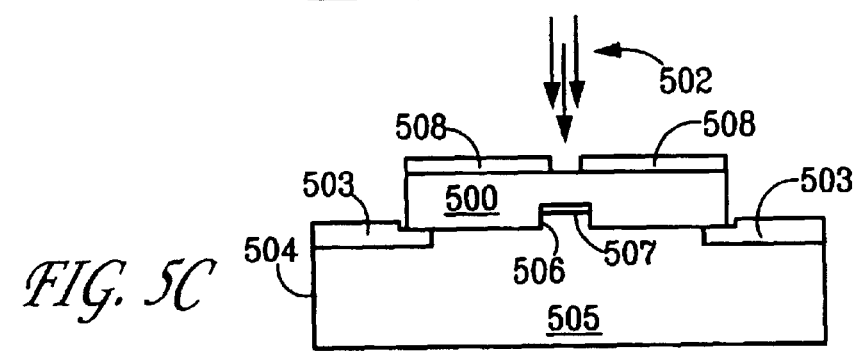
FIG. 5c shows the structure just before the chromatographic trough is Bosch etched.

As shown in FIG. 4, the next step in the process according to the instant invention is to define a chromatographic trough by masking the second surface of the silicon substrate. This structure is shown in FIG. 5c, where the silicon substrate 500 has been inverted and remounted on the substrate mount 503 in preparation for a Bosch etching step. The chromatographic trough has been defined by trough mask layer 508. For simplicity of illustration, only that portion of the chromatographic trough which is intended to intersect the fluid port 506 is defined here.

As shown in FIG. 4, the next step in the process according to the instant invention is to Bosch etch the chromatographic trench into the second surface of the silicon substrate until the stop etch layer is exposed. This step is carried out through the action of Bosch etch beam 502, as shown in FIG. 5c.

Figure 5D:
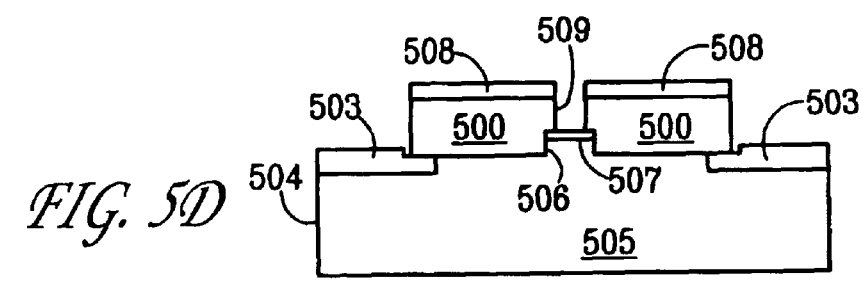
FIG. 5d shows the structure just after the chromatographic trough has been Bosch etched, and the Bosch etching process has stopped on the stop etch layer.
Figure 5E:
FIG. 5e shows the final structure of the fluid port penetrating the silicon substrate.

The structure resulting from the Bosch etching of the chromatographic trench is shown in FIG. 5d. Here Bosch etched chromatographic trench 509 extends into silicon substrate 500 until it terminates on the stop etch layer 507. Stop etch layer 507 provides a gas-tight barrier to prevent the helium cooling gas 505 from penetrating the silicon substrate, and thereby disrupting the Bosch etching of the chromatographic trench 509.

As shown in FIG. 4, the next step in the process according to the instant invention is to remove the stop etch layer. This step will typically be carried out using a wet etch process, although any process step which removes the stop etch layer without damaging the remaining structures can be used to carry out the removal of the stop etch layer. The final structure appears in FIG. 5e, where part 510 is the silicon substrate with a fluid port on a first surface providing access to a chromatographic groove on a second surface.

The specific implementations of the present invention described above are intended only to illustrate various features of the present invention. The scope of the present invention is intended to be set by the claims in view of the specification.

We claim:

1. A method for fabricating a silicon chromatographic column in a silicon substrate comprising a first surface and a second surface, said method comprising the steps of:
   a) etching a set of fluid ports into said first surface of the silicon substrate;
   b) forming an etch stop layer in the fluid ports;
   c) Bosch etching a spiral chromatographic trench into said second surface of the silicon substrate, stopping said Bosch etch when the etch stop layer in the fluid ports is exposed; and,
   d) removing the etch stop layer, thereby connecting the fluid ports to the spiral chromatographic trench.

2. The method of claim 1, wherein the step of etching a set of fluid ports is carried out by wet etching processes.

3. The method of claim 1, wherein the step of etching a set of fluid ports is carried out by Bosch etching.

4. The method of claim 1, wherein the etch stop layer consists essentially of a silicon oxide.

5. The method of claim 1, wherein the etch stop layer consists essentially of a polymer.

6. The method of claim 1, further comprising the step of oxidizing the spiral chromatographic trench following the step of removing the etch stop layer.

7. The method of claim 1, further comprising the step of attaching a glass lid to said second surface of the silicon substrate after the step of Bosch etching the spiral chromatographic trough.

8. The method of claim 7, wherein said glass lid consists essentially of Pyrex glass.

9. The method of claim 7, wherein said step of attaching a glass lid comprises an anodic bonding process.

* * * * *